(12) United States Patent
Ely

(10) Patent No.: US 8,715,212 B1
(45) Date of Patent: May 6, 2014

(54) NECK/BACK SUPPORT SYSTEM

(71) Applicant: Gregory W. Ely, Pinellas Park, FL (US)

(72) Inventor: Gregory W. Ely, Pinellas Park, FL (US)

(*) Notice: Subject to any disclaimer, the term of this patent is extended or adjusted under 35 U.S.C. 154(b) by 24 days.

(21) Appl. No.: 13/680,191

(22) Filed: Nov. 19, 2012

(51) Int. Cl.
*A61F 5/00* (2006.01)
(52) U.S. Cl.
USPC .............................................. 602/18; 602/19
(58) Field of Classification Search
CPC ....................................................... A61F 5/00
USPC .......... 128/DIG. 23, 845–846, 869, 873–874; 602/17–19, 5–6, 32, 36, 38; 607/109; 2/44–45, 310–311; 482/122, 124; 600/594–595
See application file for complete search history.

(56) References Cited

U.S. PATENT DOCUMENTS

| 2,223,276 | A | * | 11/1940 | Ward | 602/18 |
| 2,820,455 | A | * | 1/1958 | Hall | 602/18 |
| 5,141,489 | A | * | 8/1992 | Sereboff | 602/18 |
| 8,267,877 | B2 | * | 9/2012 | Sandhu | 602/18 |

* cited by examiner

*Primary Examiner* — Ophelia A Hawthorne

(57) ABSTRACT

A belt positionable around a lower back of a wearer has a first end, a second end, a center, an interior surface and an exterior surface. A neck support has a base fabricated of a rigid material covered with a padding layer of a closed cell elastomeric foam material. The base is in a cylindrical configuration with a horizontal axis. A tube assembly is formed of upper and lower tubes each having an upper end and a lower end. A lower bracket is coupled to the exterior surface of the belt at the center. The lower end of the lower tube has a lower pivot pin pivotably coupled to the lower bracket. An upper bracket is attached to the base of the neck support at an axial central extent. The upper end of the upper tube has a pivot pin pivotably coupled to the upper bracket.

5 Claims, 4 Drawing Sheets

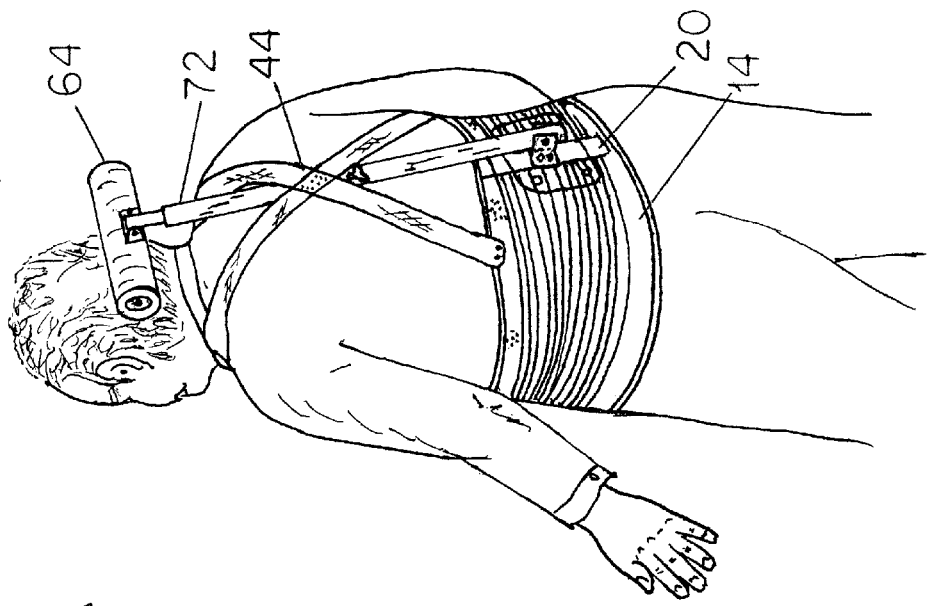
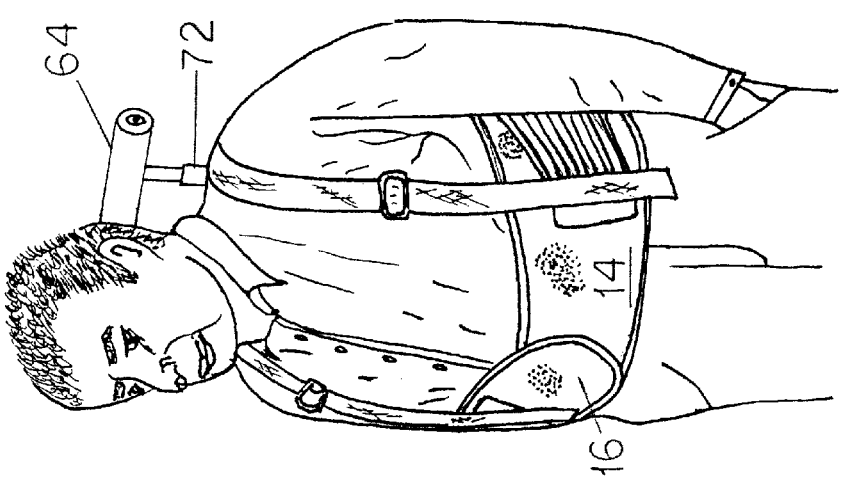

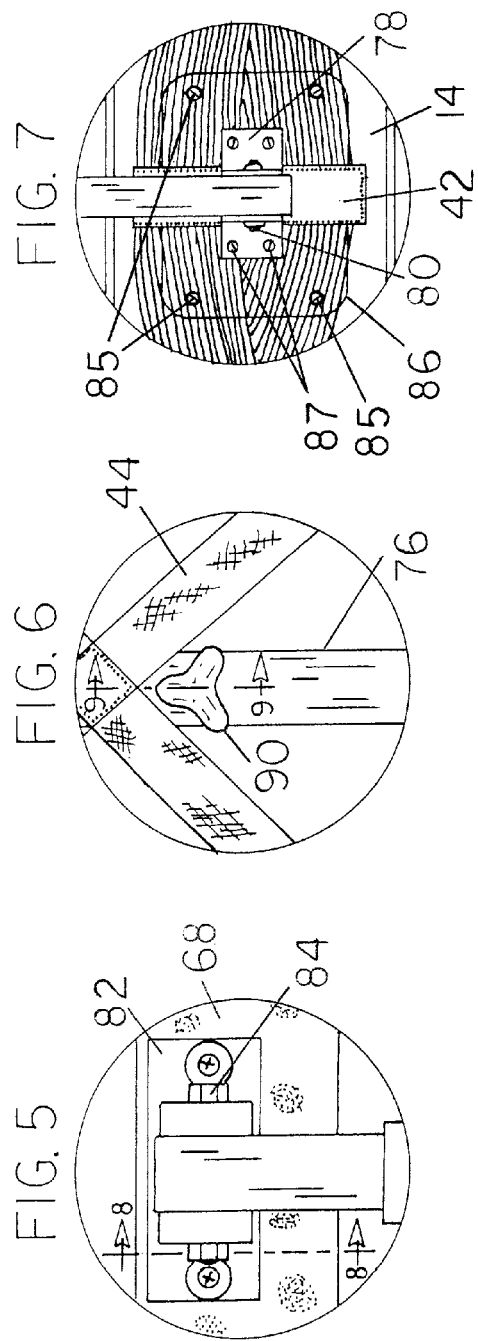
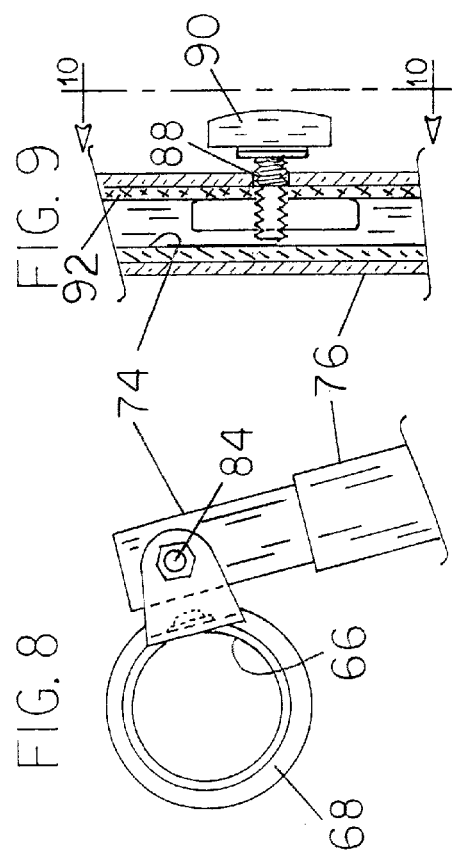

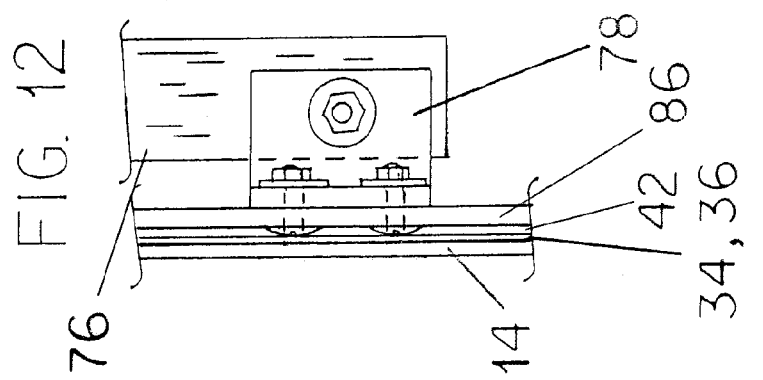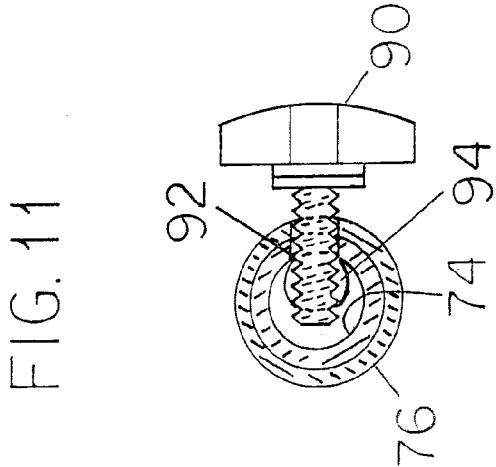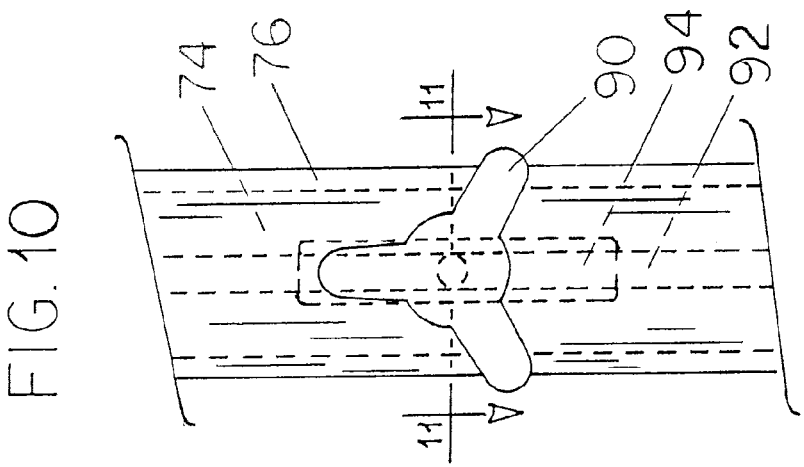

NECK/BACK SUPPORT SYSTEM

BACKGROUND OF THE INVENTION

1. Field of the Invention

The present invention relates to a neck/back support system and more particularly pertains to providing physical bracing to a neck and to a lower back of a wearer while abating adverse movement of such braced neck and lower back, the providing of bracing and the abating of adverse movement being done in a safe, reliable, convenient and economical manner.

2. Description of the Prior Art

The use of neck and back supports of known designs and configurations is known in the prior art. More specifically, neck and back supports of known designs and configurations previously devised and utilized for the purpose of supporting the neck and back of a wearer are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, they do not describe a neck/back support system that allows providing physical bracing to a neck and to a lower back of a wearer while abating adverse movement of such braced neck and lower back, the providing of bracing and the abating of adverse movement being done in a safe, reliable, convenient and economical manner.

In this respect, the neck/back support system according to the present invention substantially departs from the conventional concepts and designs of the prior art, and in doing so provides an apparatus primarily developed for the purpose of providing physical bracing to a neck and to a lower back of a wearer while abating adverse movement of such braced neck and lower back, the providing of bracing and the abating of adverse movement being done in a safe, reliable, convenient and economical manner.

Therefore, it can be appreciated that there exists a continuing need for a new and improved neck/back support system which can be used for providing physical bracing to a neck and to a lower back of a wearer while abating adverse movement of such braced neck and lower back, the providing of bracing and the abating of adverse movement being done in a safe, reliable, convenient and economical manner. In this regard, the present invention substantially fulfills this need.

SUMMARY OF THE INVENTION

In view of the foregoing disadvantages inherent in the known types of neck and back supports of known designs and configurations now present in the prior art, the present invention provides an improved neck/back support system. As such, the general purpose of the present invention, which will be described subsequently in greater detail, is to provide a new and improved neck/back support system and method which has all the advantages of the prior art and none of the disadvantages.

To attain this, the present invention essentially comprises a belt positionable around a lower back of a wearer. The belt has a first end, a second end, a center, an interior surface and an exterior surface. A neck support has a base fabricated of a rigid material covered with a padding layer of a closed cell elastomeric foam material. The base is in a cylindrical configuration with a horizontal axis. A tube assembly is formed of upper and lower tubes each having an upper end and a lower end. A lower bracket is coupled to the exterior surface of the belt at the center. The lower end of the lower tube has a lower pivot pin pivotably coupled to the lower bracket. An upper bracket is attached to the base of the neck support at an axial central extent. The upper end of the upper tube has a pivot pin pivotably coupled to the upper bracket.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved neck/back support system which has all of the advantages of the prior art neck and back supports of known designs and configurations and none of the disadvantages.

It is another object of the present invention to provide a new and improved neck/back support system which may be easily and efficiently manufactured and marketed.

It is further object of the present invention to provide a new and improved neck/back support system which is of durable and reliable constructions.

An even further object of the present invention is to provide a new and improved neck/back support system which is susceptible of a low cost of manufacture with regard to both materials and labor, and which accordingly is then susceptible of low prices of sale to the consuming public, thereby making such neck/back support system economically available to the buying public.

Lastly, it is an object of the present invention is to provide a neck/back support system for providing physical bracing to a neck and to a lower back of a wearer while abating adverse movement of such braced neck and lower back, the providing of bracing and the abating of adverse movement being done in a safe, reliable, convenient and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front perspective view of a neck/back support system constructed in accordance with the principles of the present invention.

FIG. 2 is a rear perspective view of a neck/back support system shown in FIG. 1.

FIGS. 5, 6 and 7 are enlarged showings of portions of the system taken at Circles 5, 6 and 7 of FIG. 3.

FIG. 8 is a cross sectional view taken at line 8-8 of FIG. 5.

FIG. 9 is a cross sectional view taken at line 9-9 of FIG. 6.

FIG. 10 is a cross sectional view taken at line 10-10 of FIG. 9.

FIG. 11 is a cross sectional view taken at line 11-11 of FIG. 10.

FIG. 12 is an end view taken adjacent to the lower bracket.

The same reference numerals refer to the same parts throughout the various Figures.

DESCRIPTION OF THE PREFERRED EMBODIMENT

Figure 3:
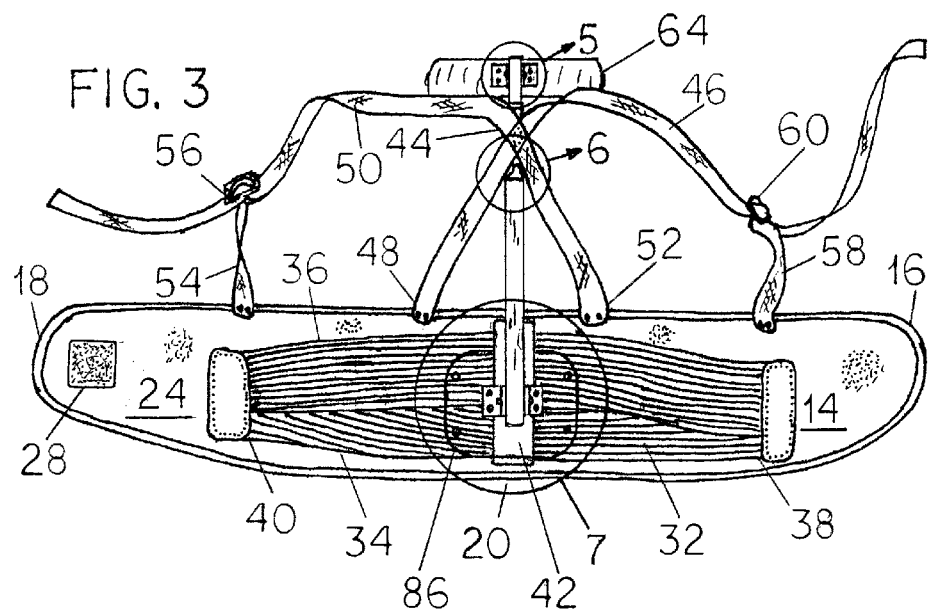
FIG. 3 is a rear elevational view of the system shown in FIGS. 1 and 2, the system not being worn.
Figure 4:
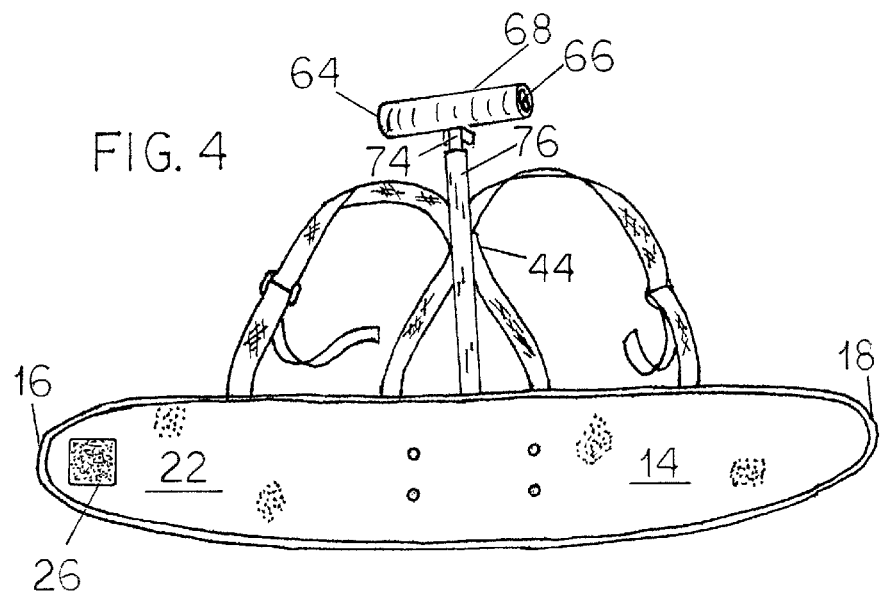
FIG. 4 is a front elevational view of the system shown in FIGS. 1, 2 and 3, the system not being worn.

With reference now to the drawings, and in particular to FIG. 1 thereof, the preferred embodiment of the new and improved neck/back support system embodying the principles and concepts of the present invention and generally designated by the reference numeral 10 will be described.

The present invention, the neck/back support system 10 is comprised of a plurality of components. Such components in their broadest context include a belt, a neck support and a tube assembly. Such components are individually configured and correlated with respect to each other so as to attain the desired objective.

The neck/back support system 10 of the present invention is for providing physical bracing to a neck and to a lower back of a wearer while abating adverse movement of such braced neck and lower back. The providing of bracing and the abating of adverse movement is done in a safe, reliable, convenient and economical manner.

First provided is a belt 14 fabricated of a flexible, essentially inextensible material. The belt has a first front end 16, a second front end 18, and a rear center 20. The belt has an interior surface 22 and an exterior surface 24. A first pile type fastener 26 is provided on the interior surface of the belt adjacent to the first front end. A second pile type fastener 28 is provided on the exterior surface of the belt adjacent to the second front end. The belt is removably positionable around the lower back of the wearer.

Next provided is a contraction assembly 32 constructed of an inner layer of elastic bands 34 and an outer layer of elastic bands 36. The inner and outer layers have first ends 38 secured to the exterior surface of the belt adjacent to the first front end of the belt. The inner and outer layers have second ends 40 secured to the exterior surface of the belt adjacent to the second front end of the belt. The inner and outer layers have a relaxed state reducing the circumference of the belt when not in use. The inner and outer layers have a tensioned state extending the circumference of the belt when worn to brace the lower back of the wearer.

Next provided is a central retaining strap 42. The central retaining strap is stitched to the elastic bands midway between the first and second ends of the inner and outer layers of the elastic bands. The elastic bands are more widely spaced from each other at the retaining strap than at the first and second ends of the inner and outer layers of the elastic bands.

A strap assembly 44 is next provided. The strap assembly includes a first long strap 46. The first long strap has a rear end 48 coupled to the exterior surface of the belt adjacent to the rear center and extending over the left shoulder of the wearer. The strap assembly includes a second long strap 50 having a rear end 52 coupled to the exterior surface of the belt adjacent to the rear center and extending over the right shoulder of the wearer. The strap assembly includes a first short strap 54 coupled to the exterior surface of the belt adjacent to the second front end with a first slider 56 adjustably receiving the first long strap. The strap assembly includes a second short strap 58 coupled to the exterior surface of the belt adjacent to the second front end with a second slider 60 adjustably receiving the second long strap. The straps are fabricated of an inextensible material. The strap assembly is adapted to hold the system at a proper elevation on the wearer during use.

Next, a cylindrical neck support 64 is provided. The neck support has a base 66 in a cylindrical configuration with a horizontal axis. The base is fabricated of a rigid metallic material. A padding layer 68 of a closed cell elastomeric foam material covers the base.

A tube assembly 72 is next provided. The tube assembly is formed of an upper tube 74 and a lower tube 76. The upper and lower tubes each have an upper end and a lower end. A lower bracket 78 is attached to the exterior surface of the belt at the rear center. The lower end of the lower tube includes a lower pivot pin 80 pivotably coupled to the lower bracket. An upper bracket 82 is attached to the base of the neck support at an axial central extent. The upper end of the upper tube includes an upper pivot pin 84 pivotably coupled to the upper bracket. The lower end of the upper tube is slidably received in the upper end of the lower tube. The upper and lower tubes have a common vertical axis.

Next provided is a lower back plate 86 in a rectangular configuration. The lower back plate overlies the retaining strap and elastic bands and belt. Four back plate bolts 85 extend through the lower back plate, retaining strap, elastic bands and belt. Four bracket bolts 87 extend through the bracket and the lower back plate.

Finally, an adjustment assembly is provided. The adjustment assembly is formed of an aperture 88 in the lower tube and a bolt 90 extending through the aperture. An axial slot 92 in the upper tube receives the bolt. A cylindrical nut 94 within the upper tube threadedly receives the bolt. The nut is within the slot. In this manner rotational movement between the upper and lower tubes is precluded. The bolt is adapted to be loosened to allow the upper tube to move axially for increasing and decreasing the distance between the belt and the neck support. The bolt is adapted to be tightened to secure the upper tube in a proper orientation of the neck brace with respect to the neck of the wearer. In this manner physical bracing is provided to a neck of the wearer while abating adverse movement of such braced neck.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A neck/back support system comprising:
   a belt having a first end, a second end and a center, the belt having an interior surface and an exterior surface, the belt being positionable around a lower back of a wearer;
   a neck support, the neck support having a base in a generally cylindrical configuration with a generally horizontal axis, the base being fabricated of a rigid material, a padding layer of a closed cell elastomeric foam material covering the base;
   a tube assembly formed of an upper tube and a lower tube, the upper and lower tubes each having an upper end and a lower end, a lower bracket coupled to the exterior surface of the belt at the center, the lower end of the lower tube including a lower pivot pin pivotably coupled to the lower bracket, an upper bracket attached to the base of the neck support at an axial central extent, the upper end of the upper tube including an upper pivot pin pivotably coupled to the upper bracket; and
   a contraction assembly constructed of an inner layer of elastic bands and an outer layer of elastic bands, the inner and outer layers having first ends secured to the exterior surface of the belt adjacent to the first end of the belt, the inner and outer layers having second ends secured to the exterior surface of the belt adjacent to the second end of the belt, the inner and outer layers having a relaxed state reducing the circumference of the belt when not in use, the inner and outer layers having a tensioned state extending the circumference of the belt when worn to brace the lower back of the wearer.

2. The system as set forth in claim 1 and further including:
   a central retaining strap stitched to the elastic bands midway between the first and second ends of the inner and outer layers of the elastic bands, the elastic bands being more widely spaced from each other at the retaining strap than at the first and second ends of the inner and outer layers of the elastic bands.

3. The system as set forth in claim 2 and further including:
   a lower back plate in a rectangular configuration overlying the retaining strap and elastic bands and belt, four back plate bolts extending through the lower back plate, retaining strap, elastic bands and belt.

4. A neck/back support system comprising:
   a belt having a first end, a second end and a center, the belt having an interior surface and an exterior surface, the belt being positionable around a lower back of a wearer;
   a neck support, the neck support having a base in a generally cylindrical configuration with a generally horizontal axis, the base being fabricated of a rigid material, a padding layer of a closed cell elastomeric foam material covering the base;
   a tube assembly formed of an upper tube and a lower tube, the upper and lower tubes each having an upper end and a lower end, a lower bracket coupled to the exterior surface of the belt at the center, the lower end of the lower tube including a lower pivot pin pivotably coupled to the lower bracket, an upper bracket attached to the base of the neck support at an axial central extent, the upper end of the upper tube including an upper pivot pin pivotably coupled to the upper bracket; and
   an adjustment assembly formed of an aperture in the lower tube and a bolt extending through the aperture, an axial slot in the upper tube receiving the bolt, a cylindrical nut within the upper tube threadedly receiving the bolt, the nut being within the slot to preclude rotational movement between the upper tube and the lower tube, the bolt adapted to be loosened to allow the upper tube to move axially for increasing and decreasing the distance between the belt and the neck support, the bolt adapted to be tightened to secure the upper tube in a proper orientation of the neck support with respect to the neck of the wearer.

5. A neck/back support system (10) for providing physical bracing to a neck and to a lower back of a wearer while abating adverse movement of such braced neck and lower back, the providing of bracing and the abating of adverse movement being done in a safe, reliable, convenient and economical manner, the system comprising, in combination:
   a belt (14) fabricated of a flexible, essentially inextensible material, the belt having a first front end (16 and a second front end (18) and a rear center (20), the belt having an interior surface (22) and an exterior surface (24), a first pile type fastener (26) on the interior surface of the belt adjacent to the first front end, a second pile type fastener (28) on the exterior surface of the belt adjacent to the second front end, the belt being removably positionable around the lower back of the wearer;
   a contraction assembly (32) constructed of an inner layer of elastic bands (34) and an outer layer of elastic bands (36), the inner and outer layers having first ends (38) secured to the exterior surface of the belt adjacent to the first front end of the belt, the inner and outer layers having second ends (40) secured to the exterior surface of the belt adjacent to the second front end of the belt, the inner and outer layers having a relaxed state reducing the circumference of the belt when not in use, the inner and outer layers having a tensioned state extending the circumference of the belt when worn to brace the lower back of the wearer;
   a central retaining strap (42) stitched to the elastic bands midway between the first and second ends of the inner and outer layers of the elastic bands, the elastic bands being more widely spaced from each other at the retaining strap than at the first and second ends of the inner and outer layers of the elastic bands;
   a strap assembly (44) including a first long strap (46) having a rear end (48) coupled to the exterior surface of the belt adjacent to the rear center and extending over the left shoulder of the wearer, the strap assembly including a second long strap (50) having a rear end (52) coupled to the exterior surface of the belt adjacent to the rear center and extending over the right shoulder of the wearer, the strap assembly including a first short strap (54) coupled to the exterior surface of the belt adjacent to the second front end with a first slider (56) adjustably receiving the first long strap, the strap assembly including a second short strap (58) coupled to the exterior surface of the belt adjacent to the second front end with a second slider (60) adjustably receiving the second long strap, the straps being fabricated of an inextensible material, the strap assembly adapted to hold the system at a proper elevation on the wearer during use;
   a cylindrical neck support (64), the neck support having a base (66) in a cylindrical configuration with a horizontal axis, the base being fabricated of a rigid metallic material, a padding layer (68) of a closed cell elastomeric foam material covering the base;

a tube assembly (72) formed of an upper tube (74) and a lower tube (76), the upper and lower tubes each having an upper end and a lower end, a lower bracket (78) attached to the exterior surface of the belt at the rear center, the lower end of the lower tube including a lower pivot pin (80) pivotably coupled to the lower bracket, an upper bracket (82) attached to the base of the neck support at an axial central extent, the upper end of the upper tube including an upper pivot pin (84) pivotably coupled to the upper bracket, the lower end of the upper tube being slidably received in the upper end of the lower tube with the upper and lower tubes having a common vertical axis;

a lower back plate (86) in a rectangular configuration overlying the retaining strap and elastic bands and belt, four back plate bolts (85) extending through the lower back plate, retaining strap, elastic bands and belt, four bracket bolts (87) extending through the bracket and the lower back plate; and an adjustment assembly formed of an aperture (88) in the lower tube and a bolt (90) extending through the aperture, an axial slot (92) in the upper tube receiving the bolt, a cylindrical nut (94) within the upper tube threadedly receiving the bolt, the nut being within the slot to preclude rotational movement between the upper and lower tubes, the bolt adapted to be loosened to allow the upper tube to move axially for increasing and decreasing the distance between the belt and the neck support, the bolt adapted to be tightened to secure the upper tube in a proper orientation of the neck support with respect to the neck of the wearer for providing physical bracing to a neck of the wearer while abating adverse movement of such braced neck.

\* \* \* \* \*